(12) United States Patent
Bauer et al.

(10) Patent No.: US 12,057,223 B2
(45) Date of Patent: Aug. 6, 2024

(54) EXTRACORPOREAL BLOOD TREATMENT SYSTEM WITH AUGMENTED REALITY DEVICE FOR CHECKING THE ASSEMBLY AND WITH FUNCTION TEST

(71) Applicant: B. Braun Avitum AG, Melsungen (DE)

(72) Inventors: Florian Bauer, Melsungen (DE); Christian Schleicher, Dipperz (DE)

(73) Assignee: B. Braun Avitum AG, Melsungen (DE)

( * ) Notice: Subject to any disclaimer, the term of this patent is extended or adjusted under 35 U.S.C. 154(b) by 353 days.

(21) Appl. No.: 17/630,683

(22) PCT Filed: Jul. 28, 2020

(86) PCT No.: PCT/EP2020/071234
§ 371 (c)(1),
(2) Date: Jan. 27, 2022

(87) PCT Pub. No.: WO2021/023574
PCT Pub. Date: Feb. 11, 2021

(65) Prior Publication Data
US 2022/0319688 A1  Oct. 6, 2022

(30) Foreign Application Priority Data

Aug. 2, 2019 (DE) ..................... 10 2019 120 999.4

(51) Int. Cl.
*G16H 40/63* (2018.01)
*A61M 1/14* (2006.01)

(52) U.S. Cl.
CPC .............. *G16H 40/63* (2018.01); *A61M 1/15* (2022.05); *A61M 2205/3306* (2013.01);
(Continued)

(58) Field of Classification Search
None
See application file for complete search history.

(56) References Cited

U.S. PATENT DOCUMENTS 10,617,288 B2   4/2020  Carlson
2014/0266983 A1*  9/2014  Christensen ........ A61M 1/1601
                                                      345/8
(Continued)

FOREIGN PATENT DOCUMENTS

DE   102014217559 A1   3/2016
DE   102015217838 A1   3/2017

OTHER PUBLICATIONS

Written Opinion received in International Application No. PCT/EP2020/071234 dated Oct. 29, 2020, with translation, 14 pages.
(Continued)

*Primary Examiner* — Lina Cordero
(74) *Attorney, Agent, or Firm* — Christopher A. Rothe; Culhane PLLC

(57) ABSTRACT

A method and a device for activating a function of a device, preferably of a medical device. The method includes the steps of: detecting an actual state of the device using a camera, preferably an AR device, which is preferably AR glasses; comparing the actual state of the device with a desired state of the device using a CPU connected to the camera; transmitting, on the basis of the comparison, a command for starting the function of the device or a function test, preferably a function test, from the CPU to the device; and activating the function or the function test of the device on the basis of this command.

12 Claims, 2 Drawing Sheets

(52) U.S. Cl.
CPC .............. *A61M 2205/3331* (2013.01); *A61M 2205/507* (2013.01); *A61M 2205/70* (2013.01); *A61M 2209/02* (2013.01)

(56) References Cited

U.S. PATENT DOCUMENTS

| | | | |
|---|---|---|---|
| 2016/0124501 A1* | 5/2016 | Lam ........................ | G06F 3/017 345/156 |
| 2016/0206800 A1* | 7/2016 | Tanenbaum ........ | A61M 1/1613 |
| 2017/0083671 A1 | 3/2017 | Benner et al. | |
| 2017/0172398 A1* | 6/2017 | Carlson ................ | A61B 90/361 |
| 2017/0172695 A1* | 6/2017 | Daniel .................... | A61M 1/16 |
| 2019/0064520 A1 | 2/2019 | Christensen | |
| 2020/0294392 A1* | 9/2020 | Peesapati ................ | A61M 1/14 |

OTHER PUBLICATIONS

Search Report received in German Application No. 10 2019 120 999.4 dated Apr. 21, 2020, with translation, 18 pages.
Search Report received in International Application No. PCT/EP2020/071234 dated Oct. 29, 2020, with translation, 7 pages.

* cited by examiner

EXTRACORPOREAL BLOOD TREATMENT SYSTEM WITH AUGMENTED REALITY DEVICE FOR CHECKING THE ASSEMBLY AND WITH FUNCTION TEST

CROSS-REFERENCES TO RELATED APPLICATIONS

This application is the United States national phase entry of International Application No. PCT/EP2020/071234, filed Jul. 28, 2020, and claims priority to German Application No. 10 2019 120 999.4, filed Aug. 2, 2019. The contents of International Application No. PCT/EP2020/071234 and German Application No. 10 2019 120 999.4 are incorporated by reference herein in their entireties.

FIELD

The disclosure relates to a method and a device for checking the function of medical apparatuses.

BACKGROUND

Augmented reality (abbreviated as AR) is the computer-assisted extension of reality perception. This information can address all human sensory modalities. However, augmented reality is often understood to mean only the visual representation of information, i.e. the addition of computer-generated supplementary information or virtual objects to images or videos by means of overlay/superimposition. In soccer broadcasts, augmented reality is the overlay of distances in the case of free kicks using a circle or a line, for example.

A dialysis apparatus/a dialysis machine allows the patient-specific removal of dissolved substances (e.g. urea, creatinine, vitamin B12 or β2-microglobulin) and, if necessary, of a defined water content from the blood in kidney replacement treatments. Dialysis apparatuses are used for both hemodialysis and hemodiafiltration. Basically, dialysis apparatuses can be divided into the following modules: Extracorporeal blood circuit, dialysis fluid circuit, disinfection unit, operating unit and power supply unit. In addition, consumable materials, so-called disposables, are used during the treatment. These disposables are e.g. dialysis fluid cannulae, blood tubing systems, dialyzers, dialysis concentrates, etc.

A disadvantage in the prior art is that caregivers need special user training to use dialysis apparatuses or to properly attach the disposables to the dialysis apparatus. This user training is necessary for each new generation of a dialysis machine.

SUMMARY

The object of the disclosure is to allow a fast, efficient and error-free application of the disposables as well as a fast and safe self-test by internal and external information.

The disclosure relates to a method for activating a function of a device, preferably a medical device, comprising the steps of:
 detecting the actual state of the device by means of a camera, preferably on an AR device, preferably AR glasses or an AR visual protection pane,
 comparing the actual state of the device with a desired/target state of the device by means of at least one CPU connected to the camera,
 transmitting, on the basis of the comparison, a command for starting a function, preferably a function test, from the CPU to the device,
 activating a function, preferably a function test, of the device on the basis of the command.

In other words, the at least one CPU/computing unit receiving the images from the camera identifies the state/set-up/setting/assembly stage of a medical device, preferably a dialysis machine. In this regard, the camera and, if applicable, also the CPU/computing unit can be housed or integrated in the AR device, preferably on smart glasses. The at least one CPU/computing unit overlays the necessary steps to be carried out by the user, e.g. for correctly connecting disposables to the medical device, into a field of view of the AR device, in particular smart glasses (preferably a projector, which is connected to the CPU, overlays the information).

When the CPU identifies via the camera arranged on the AR device that a setup has been properly completed, the CPU starts the device for a function test via a preferably wireless connection, preferably by means of wireless technology available under the registered trademark BLUETOOTH® or a wireless local area network (W-LAN) available under the registered trademark ZIGBEE®, near-field communication (NFC) or mobile radio.

Alternatively or additionally, the CPU or a data transmission device on the AR device is provided and adapted to transmit the images of the camera to another, second or fixed CPU. Preferably, this CPU is located in a medical device, but it can also be external to the AR device and/or the medical device, e.g. in the form of a PC connected to the medical device. This second or stationary CPU preferably has greater computing power than the first CPU, which, if applicable, is located on the AR device. The second CPU processes the received data and transmits processed data back to the first CPU of the data transmission device to the AR device which then causes the information to be displayed in the field of view of the AR device. In other words, the first CPU on the AR device is used to transmit the data and controls the display of information whereas the second, external or stationary CPU is used as a data processing unit as well as a computing unit for processing the captured images and derives therefrom e.g. action steps, which it returns to the first CPU as concrete information to be displayed, as described above.

Preferably, the device is a medical device and more preferably a dialysis apparatus, a dialysis machine, a syringe pump or the like.

The AR device is preferably a product of the class of wearables (wearable computing). A wearable/wearable computer is attached to the user's body or integrated into the clothing during use. Preferably, the AR device according to the disclosure has an optical display integrated in the field of view of a user as well as a CPU and/or a data transmission unit. More preferably, the AR device is a pair of AR glasses, smart glasses, smartglasses, data glasses, or a head-up display. In this context, smart glasses or smartglasses (or colloquially: data glasses) are preferably a wearable computer on a pair of glasses that adds information to the user's field of view. More preferably, the glasses also include the camera. Additionally or alternatively, the glasses can also have a data transmission unit. The glasses make possible augmented reality or mixed reality.

Preferably, the camera is a digital camera. In addition to discretely displaying information on the display of the AR device, information can also be combined with the captured image of the integrated digital camera. For this purpose, data can be directly obtained from the Internet and transmitted.

Preferably, the camera is in data connection with the first (AR device integrated) CPU and/or the second, stationary or separate CPU, preferably in a wireless fashion, e.g. via wireless technology available under the registered trademark BLUETOOTH®, W-LAN or the like. Alternatively or additionally, the first CPU on the AR device can be in data connection with a second external CPU, preferably in a wireless fashion, e.g. via Bluetooth®, W-LAN or the like. Preferably, the CPU on the AR device is in data connection with the medical device, preferably in a wireless fashion, e.g. via wireless technology available under the registered trademark BLUETOOTH®, W-LAN or the like. The second CPU is preferably a computing unit/CPU already present in the medical device for control purposes thereof.

Preferably, the comparison of the actual state of the device with a desired state of the device is carried out by means of an image analysis algorithm which is stored on a storage medium of the CPU which may be the first CPU on the AR device, or at least an optional second CPU in the medical device or external to the AR device and/or the medical device.

Preferably, the device performs a self-test/function test/pressure self-test or the like in response to the input of the camera. Here, the function test can be activated after a manual confirmation on the medical device itself, or by means of a gesture identified by the camera and the CPU, or simply after a predetermined time. For example, a pressure self-test can be started after connecting the pressure sensors. During the pressure self-test, preferably the connected/mounted disposables on the medical device are pressurized by the medical device. If a predetermined pressure drop is determined by pressure sensors, there is a leakage or a faulty connection and the medical device outputs an error message/signal.

The actual state denotes the current state to what extent the disposables are installed in the medical device at a first time T1. The desired state denotes the finished and correct state of the disposables in the medical device. Preferably, the setting-up process in which the disposables are installed in the medical device is broken down into different sub-steps which are, preferably each individually or as a whole, guided, monitored (comparison between the current actual state and the desired state of the sub-step) and then 'tested'.

The transmission of a command for starting a function, preferably a function test, from the CPU to the device on the basis of the comparison (or following the comparison) is preferably performed in the case of a positive comparison, i.e. when the actual state corresponds to the desired state. In the case of a negative comparison, i.e. when the actual state does not correspond to the desired state, a corresponding function is activated in response to the command, preferably an error message in the AR device or the medical device.

Preferably, the method is characterized in that it further includes the step of: displaying the function result in the AR device. In other words, the individual installation steps of the disposables are displayed in the AR device depending on the comparison of the actual state with the desired state. Alternatively or additionally, a result of the function test, for example the prevailing pressure in the connected disposables, can be displayed.

Preferably, the method is characterized in that the method further includes the step of: transmitting a function test result to the CPU and/or overlaying the necessary steps, preferably in the form of markings, animations and/or messages, in order to achieve the desired state of the device in the AR device. In other words, the medical device in which, for example, the second or separate or stationary CPU and/or a data transmission unit is present transmits a signal to the first CPU or data transmission unit in the AR device. Analogously, as already explained above, the result of the function (function result/function outcome) is then displayed in response to the signal of the medical device.

Preferably, the method is characterized in that it further comprises the step of: blocking further functions in the case of a negative function (in the case of a function test that turns out to be negative). In other words, if the actual state does not match the desired state, the medical device blocks further functions until the comparison is positive.

The method is preferably characterized in that a function test is a pressure test that measures a (line) pressure built up in disposables for testing purposes.

Preferably, the steps are shown graphically on a display. It is preferred to show in the AR device the required steps by means of pictorial representations which can be fully or partially animated and/or by means of writing in the user's field of view. In other words, markings, animations and/or messages can be projected into the field of view.

Preferably, the medical device is in data contact with the CPU, which can be located in the AR device, the medical device, a PC, or otherwise externally.

The disclosure further relates to a system for activating a device function, preferably a function test, having at least one camera, at least one CPU which is in data connection with the camera, and preferably at least one device, for example a medical device, in particular a dialysis machine, which in turn is or can be brought in data connection with the CPU, the CPU including a storage medium or being able to be brought in data connection with an external CPU on which the following steps are stored:

identifying an actual state of the device by means of the camera which is preferably arranged on an AR device, comparing the actual state of the device with a desired/target state of the device by the CPU connected to the camera, transmitting a command for starting a device function, preferably a device function test, (from the CPU) to the device when the actual state corresponds to a predetermined desired state, activating the device function, preferably the device function test, of the device on the basis of the command.

Preferably, the camera is attached to/in an AR device, which is provided and adapted to display the results of the function test and/or installation instructions, preferably according to the display principle of a head-up display.

The disclosure further preferably relates to a method and a device for activating a function of a device, preferably a medical device, including the steps of: identifying the actual state of the device by means of a camera which is preferably arranged on an AR device; comparing the actual state of the device with a desired state of the device by a CPU which is connected to the camera; transmitting a command for starting a device function, preferably a device function test (from the CPU) to the device when the actual state corresponds or appears to correspond to a predetermined desired state according to visual identification; activating a device function, preferably a device function test, in response (reaction) to the command.

In summary, the disclosure relates to a method for activating or performing a function test of a blood treatment device, preferably a dialysis machine, including the steps of: detecting an actual state of the blood treatment device by means of a camera which is preferably provided or mounted in/on an augmented reality device, preferably augmented reality glasses; comparing the actual state of the blood treatment device with a desired/target state of the blood treatment device by a control unit (CPU) connected to the camera; transmitting, on the basis of the comparison, a command for starting the function test from the control unit (CPU) to the blood treatment device; and activating the function test of the blood treatment device on the basis of the command.

Preferably, the method further comprises the steps of: transmitting a function test result to the control unit (CPU); and displaying the function test result in an augmented reality device.

More preferably, the method further includes the step of: overlaying in the augmented reality device still required steps to be carried out in order to achieve the desired state of the blood treatment device, preferably in the form of markings, animations and/or messages.

It is advantageous for the method to further include the step of: blocking further function tests in the case of a negative function test result.

Advantageously, the function test is a, preferably automated, self-test of the blood treatment device for checking setting-up actions performed by a user during a set-up of the blood treatment device.

Preferably, the function test is a pressure test measuring a pressure temporarily built up for test purposes in disposable products, in particular fluid lines, which are attached or provided to/in the blood treatment device.

Furthermore, the disclosure relates in summary to a system including at least one camera, at least one control unit (CPU) which is or can be brought in data connection with the camera, and at least one blood treatment device, in particular dialysis machine, which in turn is in or can be brought in data connection with the control unit (CPU), the control unit (CPU) being configured to detect an actual state of the blood treatment device by means of the camera, which is preferably provided or arranged in/on an augmented reality device, in particular augmented reality glasses or an augmented reality visual protection pane, to compare the actual state of the blood treatment device with a desired/target state of the blood treatment device, to transmit a command for starting a function test to the blood treatment device on the basis of the comparison, and to activate the function test of the blood treatment device on the basis of the command.

Preferably, the camera is attached or provided to/in an augmented reality device, the augmented reality device being configured to display a function test result and/or further steps to be carried out by a user.

More preferably, the function test is a, preferably automated, self-test of the blood treatment device for checking setting-up actions carried out by a user during a set-up of the blood treatment device.

It is advantageous for the function test to be a pressure test measuring a pressure temporarily built up for test purposes in disposable products, in particular fluid lines, which are attached or provided to/in the blood treatment device.

The present disclosure will be explained in more detail below on the basis of a preferred exemplary embodiment with reference to the accompanying drawings.

DETAILED DESCRIPTION

Figure 1:
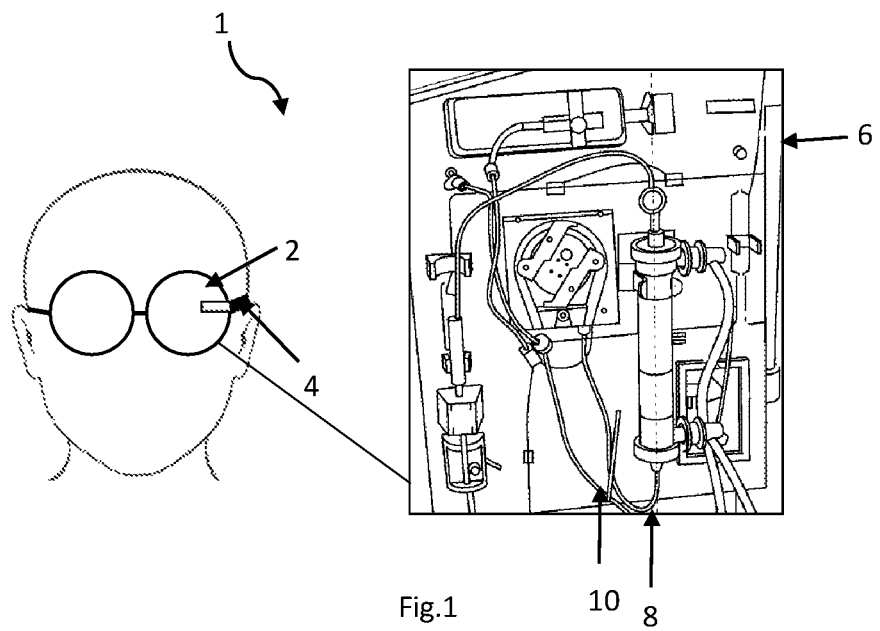
FIG. 1 shows the system for activating a function of a device according to the disclosure in a schematic diagram.

FIG. 1 shows a system 1 for activating a function or a function test of a medical device according to the disclosure in a schematic diagram. A camera 4 is attached to/in AR glasses (AR device) 2 and comprises a defined field of view 6. The field of view 6 comprises, for example, a dialysis machine 8, as a medical device, with disposables 10, which are attached thereto and which, in this case, are the lines (blood lines, dialysis fluid lines) intended for replacement and a dialyzer of the dialysis machine 8. In addition, at least one CPU is provided which is connected to the camera 4. This CPU can be a stationary, possibly device-specific computing unit or a mobile, AR glasses-specific computing unit, it being possible in the case of a stationary computing unit that the AR glasses only have a data transmission unit. The CPU (not shown) preferably in the dialysis machine 8 and/or on the AR glasses 2 identifies the actual arrangement (actual state) of the disposables 10 and compares it by means of an image analysis algorithm with a desired arrangement (desired state), which is stored in a storage medium of the CPU or which is retrieved via W-LAN. If the algorithm identifies that the disposables 10 are incorrectly/incompletely attached, a correction step in the user's field of view corresponding to the field of view 6 of the camera 4 is overlaid in the AR glasses 2. If the algorithm identifies that the disposables 10 are correctly attached, the CPU emits a command to the dialysis machine 8 to perform a function or function test, preferably by means of W-LAN or wireless technology available under the registered trademark BLUETOOTH® or the like. If the function test is positive, this is displayed on the AR glasses 2. If the function test is negative, a correspondingly required correction step is displayed on the AR glasses 2.

Figure 2:
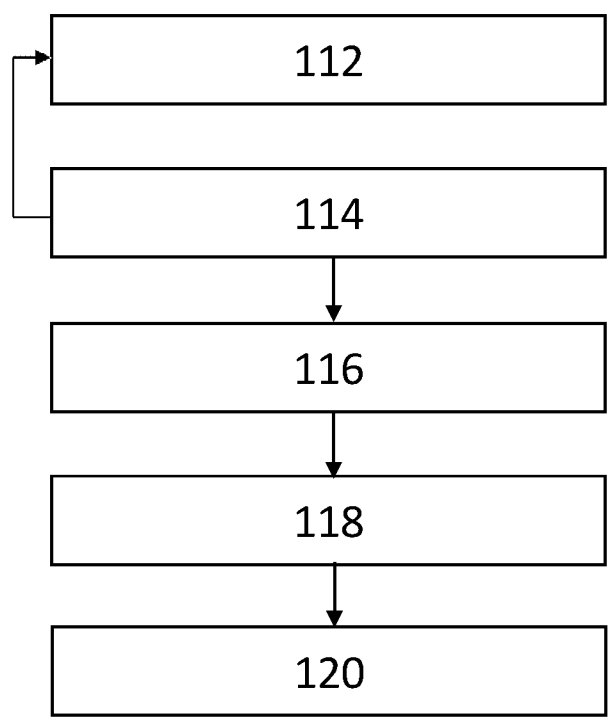
FIG. 2 shows the method for activating a function of a device.

FIG. 2 shows the method for activating a function/a function test of a device (dialysis machine 8) taking into account the above system 1.

In step 112, the camera 4 identifies the actual state of the dialysis machine 8. In other words, the camera 4 captures one or more images that display/document the current actual state.

In step 114, the CPU compares the actual state of the dialysis machine 8 with a desired state of the dialysis machine 8. In other words, the image of the camera 4 from step 112 is compared with a stored image on the CPU and pattern recognition is used to determine whether the actual state corresponds to the desired state. If such a comparison is not possible, for example due to an unsuitable image, step 112 is executed again until an image is obtained that shows the actual state and can be compared with a desired state. This repetition process or the presence of an unsuitable image can be displayed on the AR device e.g. with a preferred message/correction instruction indicating that the viewing angle needs to be changed, for example. If a comparison of the actual state with the desired state is achieved, the next step follows.

In step 116, the CPU transmits a command for starting a function test to the dialysis machine 8. In other words, once the CPU has positively compared and assessed the actual state with the desired state, a command is issued to the medical device/dialysis machine to perform a function/a function test to check whether the assembly was carried out in a functionally correct manner.

In step 118, the dialysis machine 8 performs the function or the function test. In other words, a corresponding action is carried out on the dialysis machine 8 in response to the command from the CPU.

In step 120, the dialysis machine 8 transmits the result of the function test to the CPU or the CPU measures the test result and then graphically displays the result on the AR glasses 2. Here, the result is preferably the pressure/pressure curve that prevails/was induced for test purposes in the disposables/lines.

Figure 3:
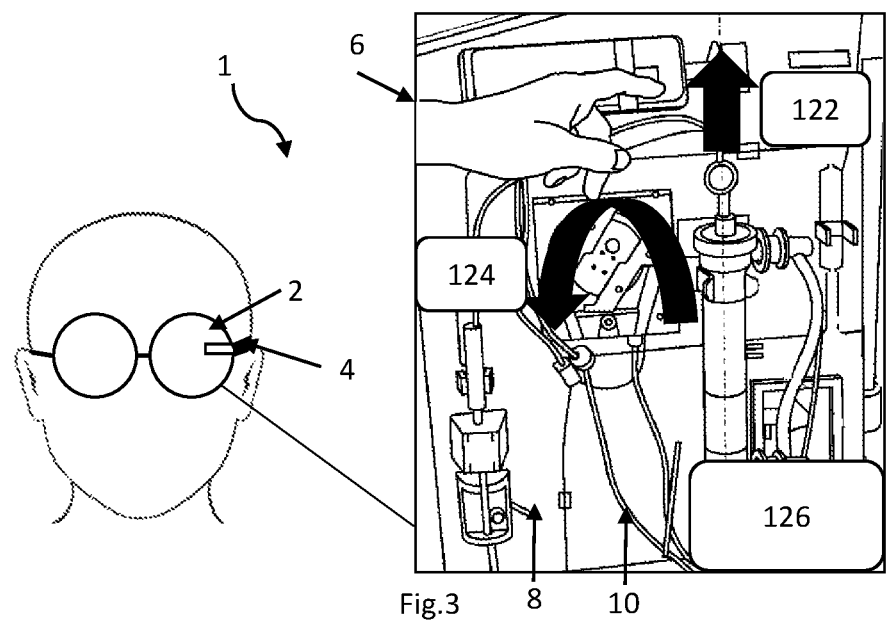
FIG. 3 shows the system for activating a function of a device according to the disclosure in a schematic diagram with an augmented reality guide.

FIG. 3 shows the system 1 for activating a function or a function test of a medical device according to the disclosure in a schematic diagram with an augmented reality guide on the basis of FIG. 2. The camera 4 is attached to the AR glasses 2 and comprises the defined field of view 6. The field of view 6 (corresponds to the diagram in FIG. 3) comprises e.g. the dialysis machine 8 (medical device) with the disposables 10 (e.g., fluid lines, tubing, dialyzer, etc.) attached thereto. Windows 122, 124 and 126 are overlaid in the field of view as well as arrows representing instructions for handling (e.g. the straight arrow next to window 122 and the semicircular arrow next to window 124). The first window 122 can contain instructions such as "Pass the tube through the connector". The second window 124 can contain instructions such as "Insert the blood tube into the blood pump as shown in the video". The third window 126 at the bottom edge can have a size different from that of one of the other windows, for example be larger, and a video can be shown in this window, for example a YouTube video.

Figure 4:
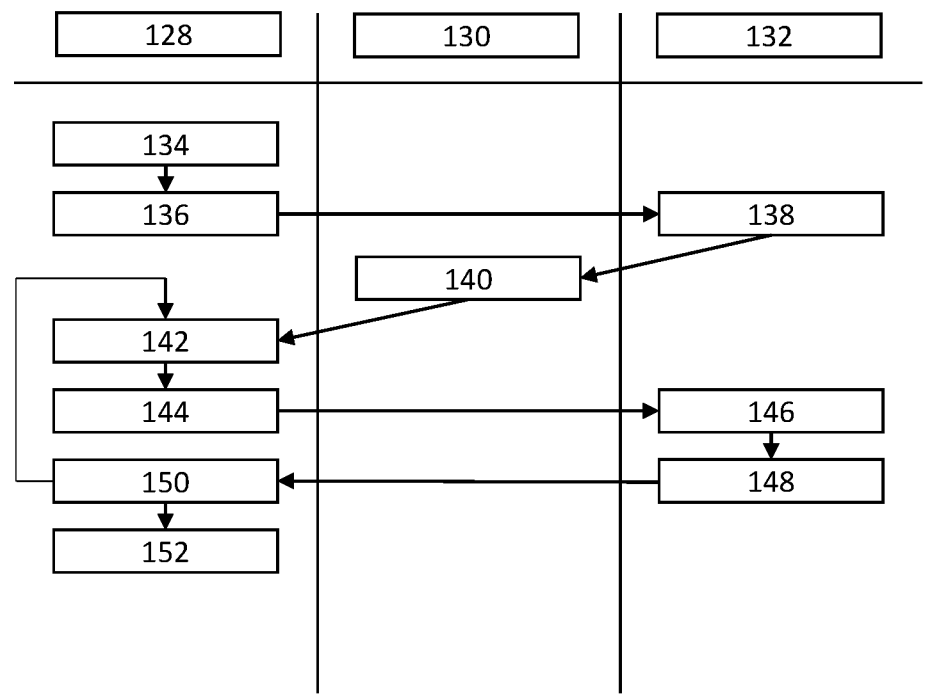
FIG. 4 shows a schematic diagram of a possible interaction between the AR device, the user and the CPU.

FIG. 4 shows a schematic diagram of a possible interaction between the AR device, the user, and the CPU. In FIG. 4, the method is divided into the method steps carried out by the AR device (see column 128), the method steps performed by the user (see column 130), and the method steps carried out by the medical device (see column 132).

In step 134, the AR device or the CPU attached thereto identifies that the task "connecting the disposables" has been identified.

In step 136, the medical device is informed that the task "connecting the disposables" has been identified.

In step 138, the medical device prepares for a function test.

In step 140, the user then installs the lines.

In step 142, the AR device identifies that the lines have been connected and can additionally or alternatively check for incorrectly connected lines.

In step 144, the medical device is informed that the disposables have been installed.

In step 146, the medical device performs a function test of the lines.

In step 148, the medical device informs the AR device about the positive test or the result.

In step 150, the result is displayed in the AR device. If the result is negative, the steps from step 142 are repeated.

If all is well, the next step is displayed in the AR device in step 152.

The invention claimed is:

1. A method for activating or performing a function test of a blood treatment device comprising the following steps:
    detecting an actual state of the blood treatment device using a camera;
    comparing the actual state of the blood treatment device with a target state of the blood treatment device using a control unit connected to the camera;
    transmitting a command to the blood treatment device to start the function test using the control unit, based on the comparison of the actual state of the blood treatment device with the target state of the blood treatment device; and
    activating the function test of the blood treatment device based on the command.

2. The method according to claim 1, further comprising the steps of:
    transmitting a function test result to the control unit; and
    displaying the function test result in an augmented reality device.

3. The method according to claim 2, further comprising the step of overlaying in the augmented reality device steps still to be performed in order to achieve the target state of the blood treatment device.

4. The method according to claim 1, further comprising the step of blocking further function tests in response to a negative function test result.

5. The method according to claim 1, wherein the function test is a self-test of the blood treatment device for checking setting-up actions performed by a user during a set-up of the blood treatment device.

6. The method according to claim 1, wherein the function test is a pressure test measuring a pressure temporarily built up for test purposes in disposable products which are attached to or provided in the blood treatment device.

7. The method according to claim 1, wherein the camera is provided in or attached to an augmented reality device.

8. A system comprising at least one camera, at least one control unit configured to be brought in data connection with the at least one camera, and at least one blood treatment device configured to be brought in data connection with the at least one control unit, wherein the at least one control unit is configured to:
    detect an actual state of the at least one blood treatment device with the at least one camera;
    compare the actual state of the at least one blood treatment device with a target state of the at least one blood treatment device;
    transmit a command for starting a function test to the at least one blood treatment device based on the comparison of the actual state of the at least one blood treatment device with the target state of the at least one blood treatment device; and
    activate the function test of the at least one blood treatment device based on the command.

9. The system according to claim 8, wherein the at least one camera is attached to or provided in an augmented reality device, the augmented reality device being configured to display at least one of a function test result and further steps to be performed by a user.

10. The system according to claim 8, wherein the function test is a self-test of the at least one blood treatment device for checking setting-up actions performed by a user when setting-up the at least one blood treatment device.

11. The system according to claim 8, wherein the function test is a pressure test measuring a pressure temporarily built up for test purposes in disposable products, which are attached to or provided in the at least one blood treatment device.

12. The system according to claim 8, wherein the at least one camera is provided in or attached to an augmented reality device.

* * * * *